US006666824B2

(12) United States Patent
Rust et al.

(10) Patent No.: US 6,666,824 B2
(45) Date of Patent: Dec. 23, 2003

(54) SYSTEM AND METHOD OF DYNAMIC AUTOMATIC SENSING OF AVAILABLE DYNAMIC RANGE

(75) Inventors: David Rust, Seattle, WA (US); David Roundhill, Woodinville, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/114,728

(22) Filed: Apr. 1, 2002

(65) Prior Publication Data

US 2003/0187354 A1 Oct. 2, 2003

(51) Int. Cl.[7] .................................................. A61B 8/00
(52) U.S. Cl. ...................................................... 600/443
(58) Field of Search ................................ 600/437–471; 73/618–635; 367/7, 11, 130, 138; 128/916

(56) References Cited

U.S. PATENT DOCUMENTS

| 5,394,750 A | * | 3/1995 | Matzuk ......................... 73/629 |
| 5,456,255 A | * | 10/1995 | Abe et al. ..................... 600/443 |
| 5,579,768 A | | 12/1996 | Klesenski |
| 5,935,074 A | * | 8/1999 | Mo et al. ...................... 600/454 |
| 5,993,392 A | | 11/1999 | Roundhill et al. |
| 6,102,859 A | * | 8/2000 | Mo ............................... 600/443 |
| 6,120,446 A | | 9/2000 | Ji et al. |
| 6,126,605 A | * | 10/2000 | Washburn et al. ............ 600/454 |
| 6,142,943 A | * | 11/2000 | Mo et al. ...................... 600/447 |
| 6,162,176 A | | 12/2000 | Washburn et al. |
| 6,176,828 B1 | * | 1/2001 | Becker et al. ................ 600/440 |
| 6,358,205 B1 | | 3/2002 | Ustuner et al. |
| 6,398,733 B1 | * | 6/2002 | Simopoulos et al. ......... 600/443 |
| 6,579,238 B1 | * | 6/2003 | Simopoulos et al. ......... 600/443 |
| 2003/0013959 A1 | * | 1/2003 | Grunwald et al. ............ 600/437 |

* cited by examiner

*Primary Examiner*—Ali M. Imam
(74) *Attorney, Agent, or Firm*—Dorsey & Whitney LLP (57) ABSTRACT

An ultrasonic diagnostic imaging system processes echo information signals by means of detecting, for different regions of the patient's anatomy, the actual noise present for that particular examination, under existing environmental conditions, and in imaging system itself. The noise detected is used to create an actual noise signature for the actual noise present in that particular examination under existing environmental conditions and in the imaging system itself, and the noise signature is used to maximize available dynamic range to create the highest resolution scan images possible while rejecting noise. In a preferred embodiment the dynamic range and noise rejection level are varied for different regions of a patient's anatomy as a function of all scanning coordinates being used, including varying depths, steering angles, and linear positions for both sector-type and linear-type scans.

24 Claims, 8 Drawing Sheets

SYSTEM AND METHOD OF DYNAMIC AUTOMATIC SENSING OF AVAILABLE DYNAMIC RANGE

TECHNICAL FIELD

This invention relates to the acquisition and display of medical ultrasonic image data. In particular, the present invention relates to altering the dynamic range used to process image data, as a function of noise actually detected in scanning particular regions of a patient's body, to achieve the best possible results in imaging the patient.

BACKGROUND OF THE INVENTION

Ultrasonic imaging technology has been a tremendous boon to the medical field. Ultrasonic imaging allows physicians to examine patients' internal tissues and organs without resorting to the use of ionizing radiation or invasive exploratory surgery. As a result, ultrasonic imaging is a very important diagnostic technology for, among many other applications, reviewing fetal development and recovery from injuries which require frequent internal examinations.

As is well known, in ultrasonic imaging, a series of high-frequency sonic pulses are generated, and these pulses "bounce" off various objects in their path. Specifically, different structures in a patient's body exhibit different levels of impedance, and ultrasonic echoes are generated when the ultrasonic signals contact impedance boundaries between these structures. The interval between the emission of the pulses and the receipt of the corresponding echoes is measured to determine the distance between the source of the pulse and the impedance boundary from which the echo resulted. In addition, the relative intensity of the echo conveys information regarding the nature of the tissues causing the echoes. Different tissues exhibit different levels of impedance to the ultrasonic signals. Therefore, varying impedance differentials exist, for example, at the boundary between muscle tissue and bone as opposed to the boundary between fatty tissue and bone. As a result, when an ultrasonic pulse strikes the impedance boundary between muscle tissue and bone, a more robust echo is generated than the echo generated when an ultrasonic pulse strikes the impedance boundary between fatty tissue and organ tissue. Ultimately, it is the mosaic assembled from each of these echoes received, reflecting the position and the nature of the objects causing the echoes, that constitutes the multi-dimensional images obtained through the use of ultrasonic imaging.

More specifically, ultrasonic images typically are generated from echoes of transmitted ultrasonic imaging pulses at a frequency of between 500,000 Hz to 15 MHz. The speed of ultrasonic waves in the body is on the order of 1,540 meters per second. The time between the generation of each pulse and its echo is used to determine the distance from the source of the pulse to the source of the echo. Rapid generation of these pulses permits the interrogation of an entire region to build a detailed image.

Figure 1:
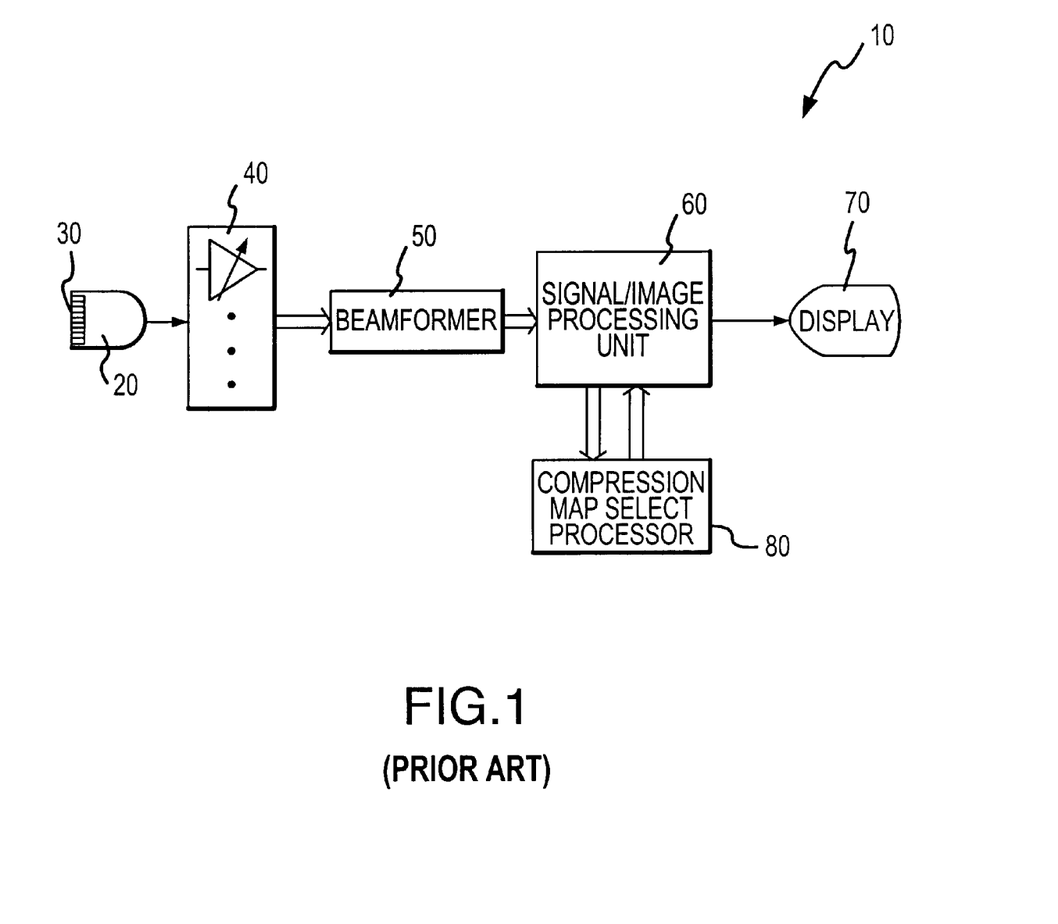
FIG. 1 is a block diagram of a prior art ultrasonic diagnostic imaging system.

FIG. 1 displays a prior art ultrasonic imaging system 10. At the front end of the system is a scanhead 20 having a linear array of transducer elements 30 coupled to associated time gain control amplifiers 40 and directed by a beamformer 50. These devices are responsible for selectively generating the ultrasonic imaging pulses, transmitting them to the patient, receiving the echoes returned, amplifying the returned echo signals as appropriate, and combining signals corresponding to the echoes to effectively form beams focused to selected regions of the patient's body. Once the signals representing the echoes are received and amplified, the signals are processed by a signal/image processing unit 60. The signal/image processing unit 60 receives the amplified echo signals and assembles them into an image of the patient's internal anatomy. Finally, the image formed by the signal/image processing unit 60 is presented on a display 70. The system might include additional devices, such as storage devices and possibly other output devices (not shown). These supplemental devices allow the results of the scans to be stored and reviewed at a later time. The system 10 also includes a compression map select processor 80, the function of which will be subsequently explained.

This is a simplified rendering of the ultrasonic imaging process; there are many problems that must be overcome for the ultrasonic system to generate a useful image having sufficient resolution to help a medical professional assess the portion of the patient's body being studied. Some of these problems can be addressed by actually manipulating the patient. For example, because ultrasonic waves do not penetrate gaseous regions well, it is difficult to image any structure behind or beneath a lung or an empty gastrointestinal tract. A physician can mitigate the problem of an empty gastrointestinal tract by requiring the patient to consume a significant amount of fluid without eliminating until after the imaging has taken place.

Other problems, however, are not quite so easily solved. Of these, perhaps the largest single problem is that of noise. In any system, the signal of interest subsists against a background of ambient signals. These other signals have nothing to do with the signal of interest, other than the fact that these unwanted signals interfere with the signal of interest. These ambient signals constitute a noise component. Furthermore, some external noise sources, such as electrical equipment used proximally to the ultrasonic imaging equipment, may introduce noise into the signal path. In addition, as a result of electrons moving through the components of the imaging system itself, the imaging system will exhibit thermal noise. For example, the noise level varies with the phasing of the transducer elements 30 of the scanhead 20 used to generate and direct ultrasonic pulses or receive the echoes of those pulses.

Both the noise and the desired signals are detected by the ultrasonic imaging system 10. Unfortunately, if the noise were to be analyzed as though it were part of the desired signal, the resulting ultrasonic image would be compromised, and the image then would inaccurately portray structures in the patient's anatomy. To avoid the noise unduly compromising the integrity of the desired signals, the desired signals must be separated from the noise, or the noise must be suppressed as much as practical. There are several mechanisms for reducing noise present in the image, including filtering the received spectrum to consider only frequencies of interest. To the extent noise exists within the spectra of the frequencies of interest, however, frequency filtering does little or nothing to separate the noise from the signals of interest.

Another way to preserve the integrity of the signal, when the magnitude of the desired signals exceeds that of the noise, is to adjust the dynamic range used in mapping the signal to the display 70 of the system 10 through the use of a mapping function referred to as a compression map. As is well known, the dynamic range is an expression of the ratio of the received magnitudes of the largest signal to that of the smallest discernible signal. Dynamic range also commonly known as the signal-to-noise ratio. Dynamic range is typically expressed as a logarithm of a ratio, expressed in units of decibels (dB). Reducing or compressing the dynamic range, in effect, involves cutting off signals having a magnitude below a predetermined value. The dynamic range can be compressed by programming the signal/image processing unit 60 to disregard signals having a magnitude below a certain level so that these unwanted signals do not unduly compromise images shown on the display 70. If the magnitude of the useful component of the signals conveying information about the patient's tissues is largely greater than the magnitude of the noise component, the noise component can be partially or completely suppressed, leaving a useful signal largely free of noise from which an image can be derived.

However, if the dynamic range is compressed too much, it detracts from the ability to process desired signals. The problem is relatively insignificant when there is relatively little noise present, because suppressing lower magnitude noise signals still allows the system to process desired signals over a larger useable dynamic range. However, as the magnitude of the noise increases, desirable signals will be increasingly affected and "drowned out" by the noise. As the dynamic range is increasingly compressed to avoid the increased noise, unfortunately, desirable signals having magnitudes comparable to the magnitude of the noise also will be lost.

Problems caused by compressing the dynamic range too much become more of a concern as the ultrasonic imaging system 10 targets regions of the patient's body at increasingly greater distances from the scanhead 20. As is well known in the art, different regions of a patient's body can be scanned and imaged by manipulating the beamformer 50, which in turn manipulates the transducers 30, the pulses they emit, and the signals they generate, to interrogate regions of the patient's body at different distances and in different directions relative to the scanhead 20. The coordinates of the region scanned in such a three-dimensional space can be defined by three variables, z, η, and N, where z represents the depth or linear distance from the scanhead 20. As also is known in the art, ultrasonic scans generally are of two forms: sector-type scans, and linear-type scans. In a sector-type scan, the direction of the interrogation is defined by two angles, η and N, where η can be regarded is the angular direction of the interrogation in the plane perpendicular to the transducer, and N is the angular direction of the interrogation from a physical axis of the transducer. In a linear-type scan, the direction of the interrogation is defined by an angle η and a linear dimension N, where η is the angular direction of the interrogation in a plane perpendicular to the linear motion of the scanhead, and N is a linear displacement from the scanhead. These scanning coordinates, z, η, and N, therefore, determine the three-dimensional position of the region of the patient's body being interrogated.

Figure 1B:
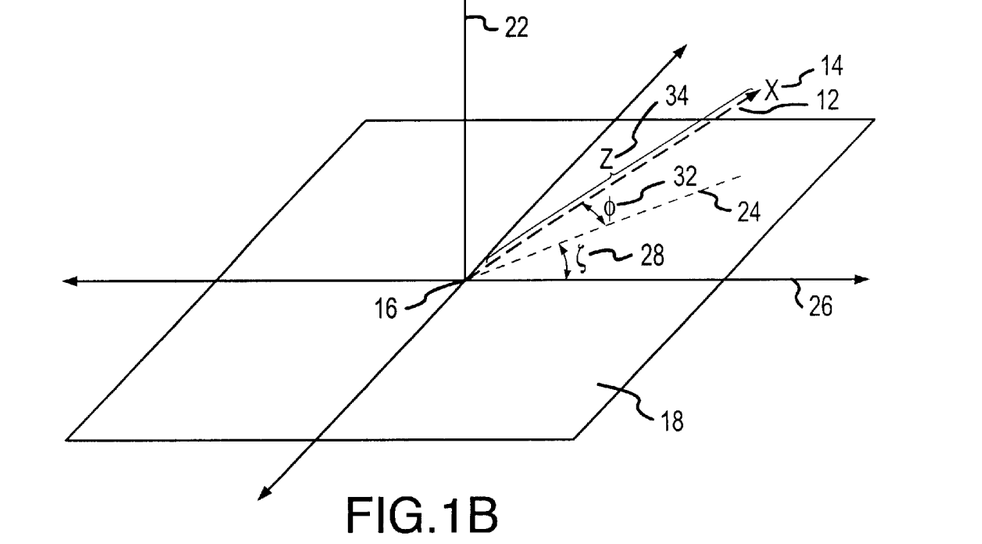
FIG. 1B is a coordinate diagram of a sector-type scan.
Figure 1C:
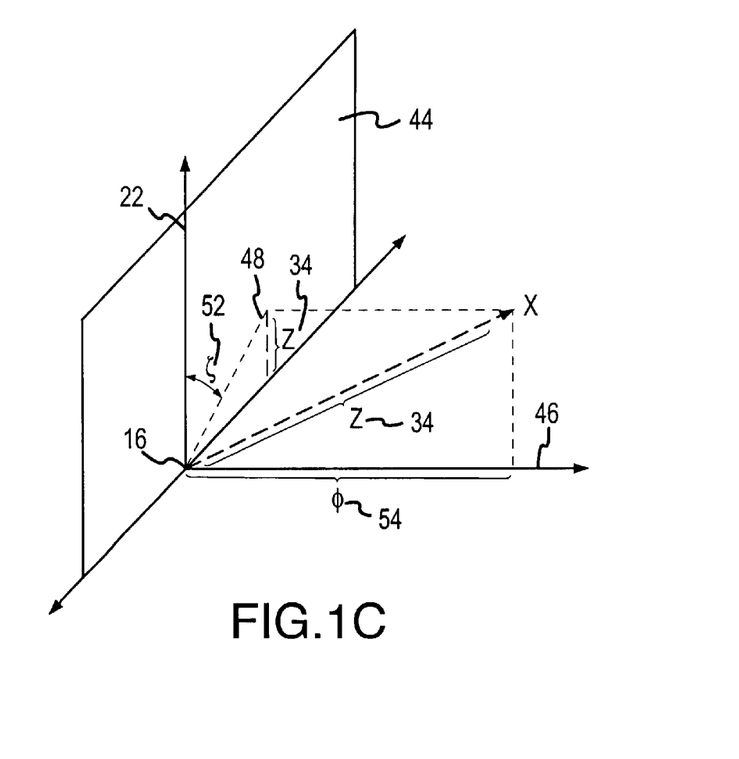
FIG. 1C is a coordinate diagram of a linear-type scan.

FIG. 1B and 1C illustrate how these scanning coordinates define the location of the region of interest. In each figure, equivalent features are numbered identically to clarify the similarities between the figures. FIG. 1B depicts a coordinate system used in a sector-type scan. Corresponding to a ray 12 to the point of interest x 14 from a point of origin 16, in the plane 18 perpendicular to the axis 22 of the transducer, is a projection 24 in the plane 18. Between the projection 24 and a base axis 26 in the plane 18 is the angle η 28, one of the two angular coordinates of the point of interest x 14. From the plane 18 to the ray 12 is the other angular coordinate N 32. The point of interest x 14 is located at a depth z 34 from the point of origin 16. FIG. 1C depicts the coordinate system used in a linear-type scan. Corresponding to the ray 12 to the point of interest x 14 from a point of origin 16, in a plane 44 perpendicular to the linear axis 46 of the transducer, is a projection 48 in the plane 44. Between the projection 48 and the axis of the transducer 22 in the plane 44 is the angle η 52, the angular coordinate of the point of interest x 14. Projecting the ray 12 onto the linear axis 46 is a projection having a length N, one of the linear coordinates of the point of interest x 14. The point of interest 14 again is located at a depth z 34 from the point of origin 16. Therefore, FIGS. 1B and 1C illustrate how the scanning coordinates η, N, define in a sector-type or a linear-type scan, respectively, the location of a point or region of interest.

The problems with overly compressing the dynamic range arise because, as the ultrasonic interrogation is directed to regions at increasingly greater distances from the scanhead 20, as defined by the scanning coordinates η, N, and z, the magnitude of the original ultrasonic signals and the resulting echoes travel through increasingly greater thicknesses of a patient's tissues. As the signals pass through more and more tissue, the magnitude of the signals becomes attenuated. The time gain control amplifiers 40 apply greater gain to signals representing echoes received from greater distances to compensate for the attenuation in magnitude of these signals. Unfortunately, however, amplifying the signals also amplifies the noise attending the desired signals, and the magnitude of the noise increases. As the time gain control amplifiers 40 apply more and more gain to signals representing echoes from greater and greater distances, the magnitude of the noise increasingly approaches the magnitude of the desired signals. Accordingly, if the dynamic range is further compressed to reject noise of ever-increasing magnitude, lower magnitude components of desired signals will be suppressed along with the noise. Compressing the dynamic range too much, therefore, results in the rejection of desired signals which, like noise, compromises the resulting image.

Figure 2:
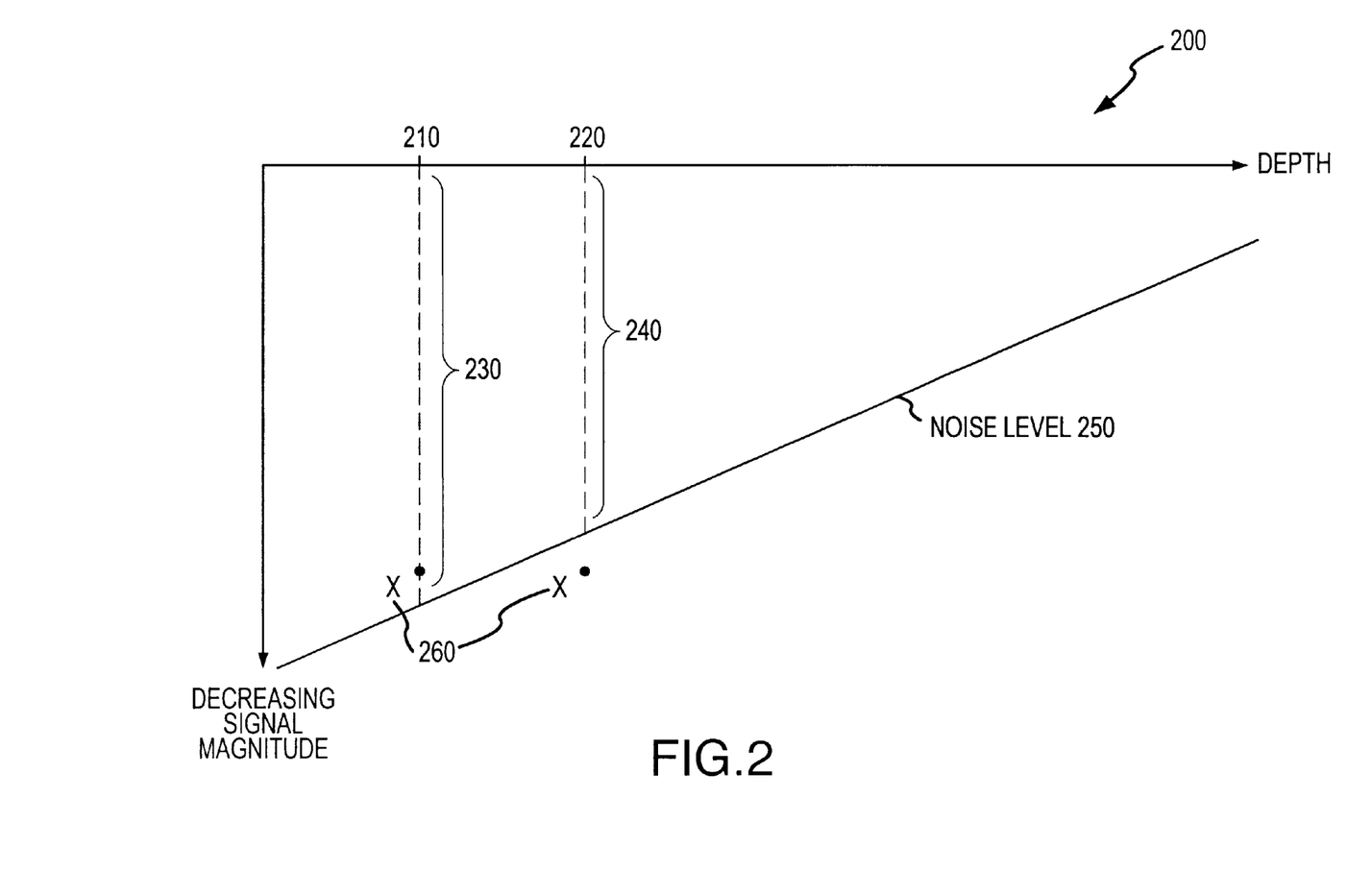
FIG. 2 is a graph illustrating how the noise level reduces the available dynamic range.

The problem presented of how compressing the dynamic range too much ultimately begins to eliminate or obscure the desired signal is illustrated by FIG. 2. FIG. 2 is an idealized graph 200 of signal levels, including a noise signal level, as a function of the depth of an ultrasonic interrogation pass. As shown in FIG. 2, the noise level 250 increases with increased depth of the interrogation pass. As was previously described and is well known in the art, time gain compensation amplifiers 40 (FIG. 1) are used to amplify signals representing echoes returned from greater scanning depths to adjust for the attenuation of the emitted ultrasonic pulses and resulting echoes as they pass through increasingly more and more of the patient's tissues. At depth 210 in the body being interrogated, there is a large dynamic range between the signals with the greatest and smallest magnitudes which can be discerned beyond the noise threshold, because a desirable low magnitude signal of magnitude X 260 still is above the threshold of the noise level 250. However, at depth 220, the threshold of the noise level 250 has increased, and the magnitude of the noise exceeds the that of the desirable signal X 260. As a result, the desirable signal of magnitude of X 260 is enveloped in the noise, and cannot be discerned over the noise. If, at depth 220, the dynamic range was extended to include the desirable signal of magnitude X 260, the noise would compromise the integrity of the data represented by the signals.

Accordingly, the theoretically optimum dynamic range is that which encompasses desirable signals of the lowest possible magnitude down to, but not including, the threshold of the noise level 250. Practically, the optimum dynamic range is that which only slightly overlaps the threshold of the noise level 250, such that the operator of the system can detect a negligible amount of noise to be assured that the dynamic range selected is not so conservative that useable signals are being suppressed. In either case, the system can work with the greatest useful dynamic range to present the best image possible, without the integrity of the image being unduly compromised by the attendant noise. Thus, at 210, the theoretically ideal dynamic range would include the range signified by the line 230. By contrast, at 220, because of the increased noise, a smaller theoretically ideal dynamic range is possible signified by the line 240. Practically, the optimal dynamic range in each case would be slightly greater.

Figure 3:
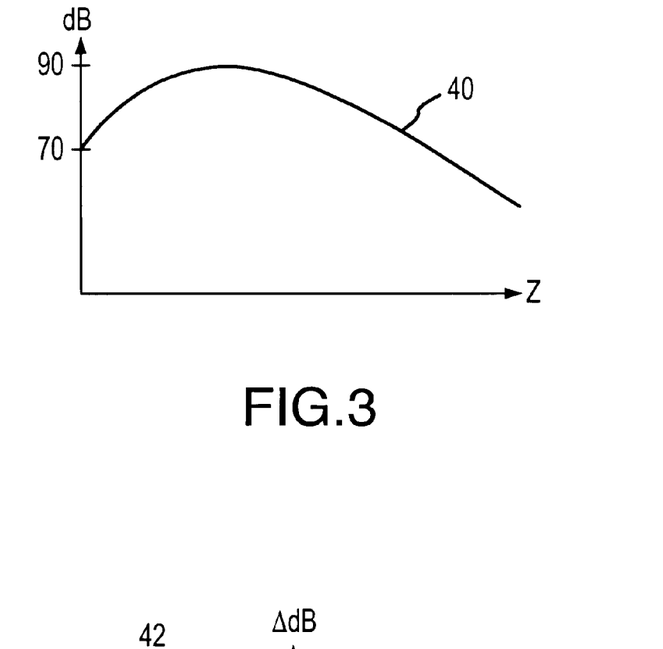
FIG. 3 is a graph illustrating an exemplary variation of the signal dynamic range of an ultrasonic image with increasing scan depth.
Figure 4:
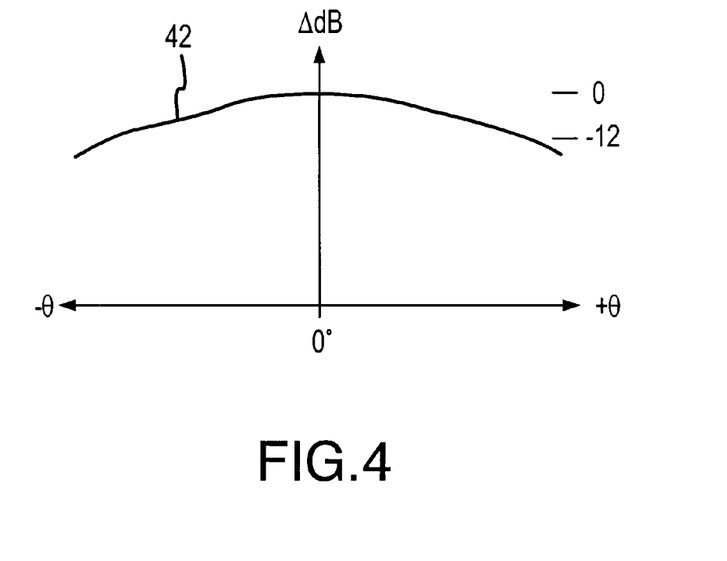
FIG. 4 is a graph illustrating an exemplary variation of the signal dynamic range of an ultrasonic image with increasing steering angle in a sector-type scan.

Not surprisingly, noise varies not only with scan depth as in the simplified conception illustrated in FIG. 2, but noise also varies as the ultrasonic imaging system 10 (FIG. 1) interrogates other regions of interest as defined by depth and other changing scanning coordinates. FIGS. 3 and 4 illustrate the degradation in signal to noise ratio with changes in depth and steering angle for a sector-type scan. With reference to FIG. 1B, the graphs of FIGS. 3 and 4 would correspond to a situation where, for example, η 28 remains constant, while N 32 and z 34 change. FIG. 3 shows that, as depth increases, the signal to noise ratio initially improves slightly, but then begins to decrease with increasing depth. The signal to noise ratio degrades because, as depth of the scan increases, additional gain must be applied by the time gain amplifiers 40 (FIG. 1) to make up for attenuation of the ultrasound signals passing through greater thicknesses of a patient's tissue. Application of additional gain amplifies the noise as well as the desired signal, reducing the useable dynamic range. FIG. 4 shows that the signal to noise ratio, after remaining somewhat level as the steering angle begins to increase, begins to degrade more sharply as the angle becomes more and more oblique. Again, as a result of the steering angle becoming more extreme, additional gain must be applied to compensate for signal attenuation, which amplifies the noise and reduces the useable dynamic range. Therefore, as FIGS. 3 and 4 show, to process signals to take advantage of the greatest useable dynamic range, the dynamic range would have to be adjusted for different regions of the patient being scanned.

To exploit the largest useable dynamic range, the signal/image processing unit 60 (FIG. 1) of the ultrasonic imaging system 10 can be programmed to select a preprogrammed dynamic range for different regions of the patient's anatomy as a function of changing scanning coordinates. This technology is described in U.S. Pat. No. 5,993,392, entitled "Variable Compression of Ultrasonic Image Data with Depth and Lateral Scan Dimensions," which is incorporated herein by reference. The system described adjusts the dynamic range used in processing the signals resulting from the ultrasonic echoes in response to varying noise levels expected at different regions in the patient's anatomy relative to the scanhead 20 as a function of changing scanning coordinates. Specifically, the system employs a compression map select processor 80 referenced by the signal/image processing unit 60 to select the estimated optimal usable dynamic range corresponding to the region of the patient presently being interrogated as a function of the scanning coordinates identifying that region. The compression map is created based on empirical evidence from prior scans to predict the level of noise expected at various regions of the patient's anatomy as defined by the scanning coordinates.

Figure 5:
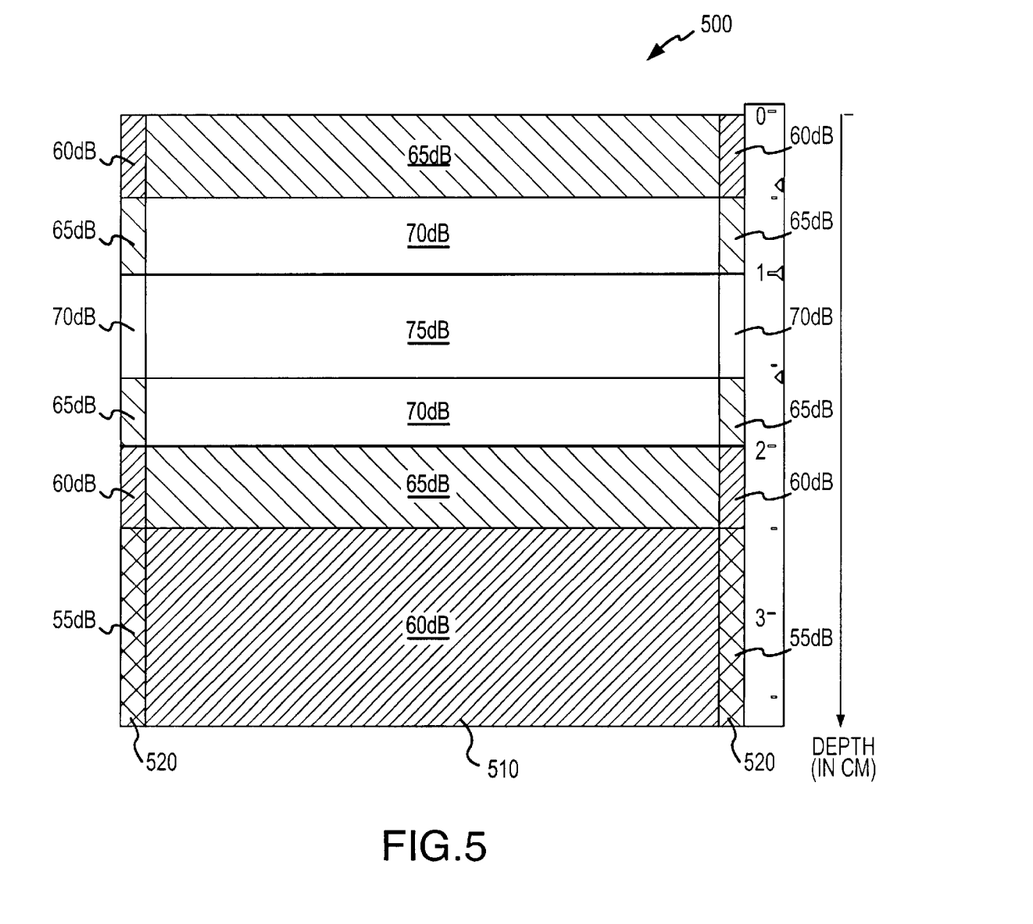
FIG. 5 is a dynamic range map for a prior art ultrasonic imaging system adapted to adjust its dynamic range depending on the depth and linear position in a linear-type scan.

FIG. 5 shows a sample compression map 500 of the type provided by the system described in U.S. Pat. No. 5,993,392. The compression map 500 shows the dynamic range to which the actual range of received signals is to be compressed as a function of changing depths and lateral dimensions for a linear-type scan. The compression map 500 is based on empirically-derived estimates of what noise is expected with changes in these scanning variables. The central region 510 of the compression map 500 shows how the dynamic range varies with changing scan depth within a certain centralized range. For example, from the most shallow depth to the greatest depth, the dynamic range changes from 65 dB, at a depth of 0 cm to 0.5 cm, to 60 dB at a depth of 2.5 cm to 3.5 cm. However, outside the central range of the patient's body, for which the appropriate dynamic range is indicated by the central region 510 of the compression map 500, different dynamic ranges are used. The appropriate dynamic ranges for these linear extremes is depicted in the outlying regions 520 of the compression map 500. In these outlying regions 520 of the compression map, the dynamic range changes from 60 dB, at a depth of 0 cm to 0.5 cm, to 55 dB, at a depth of 2.5 cm to 3.5 cm. The compression map, therefore, allows for the system to compress the dynamic range as little as possible as different regions of the patient's anatomy are being interrogated, while still suppressing compromising noise signals. A similar compression map can be constructed for a sector-type scan, adapting the dynamic range for varying scanning depths and steering angles. Returning to FIG. 1, the compression map select processor 80 is used to incorporate the projected maximum available dynamic range for regions as defined by the current scanning coordinates, and compress the dynamic range used to that level.

However, the ultrasonic imaging system 10 shown in FIG. 1 does not necessarily optimize the actual available dynamic range in all cases, because the compression map 500 (FIG. 5) employed by the compression map select processor 80 (FIG. 1) dictates to what dynamic range the actual signals should be compressed under typical imaging conditions. Because it is a predictive technology which compresses the dynamic range based on a typical, expected noise level, it does not adjust the dynamic range when the actual noise level exceeds or falls short of the predicted level. Thus, the scans of some patients will return signals having more or less noise than generally anticipated for scans at the region defined by the scanning coordinates. The atypical magnitude of noise might be as a result of the external conditions, such as other electrical equipment used proximally to the ultrasonic imaging equipment, as a function of thermal noise generated within the ultrasonic imaging system itself, or as a result of other unforeseen factors. As a result, if the predicted available dynamic range is too great or too small, then the noise will cause the system to present a noise-compromised image or unnecessarily restrict the potential clarity of the ultrasonic images, respectively. Naturally, it is best to set the preprogrammed dynamic range conservatively so that the noise impinges only on the periphery of that dynamic range. Unfortunately, the obvious disadvantage to this conservative preprogramming is that potentially useable—and useful—dynamic range goes unused, resulting in a scan having a resolution less than what it ideally could have.

There is therefore a need for an ultrasonic imaging system that can maximize the available dynamic range for the ultrasonic imaging of any particular patient.

SUMMARY OF THE INVENTION

The present invention is directed to a system and method that improves the clarity of images generated by ultrasonic imaging techniques by maximizing the available dynamic range applied in processing the signals. The present invention maximizes the available dynamic range based not just on the noise expected at particular regions of the patient's anatomy, but on the actual noise detected. According to one aspect of the present invention, actual noise present in particular regions of the patient's anatomy is sensed by passively monitoring the noise detected. From the noise actually detected in the different regions of the patient's anatomy, an actual noise function is generated. Then, optionally using a low pass filter to created a smoothly-varying function of measured noise function, this actual noise function—instead of an expected noise function—is used to select the greatest available dynamic range to generate the clearest possible ultrasonic images.

DETAILED DESCRIPTION OF THE INVENTION

Figure 6:
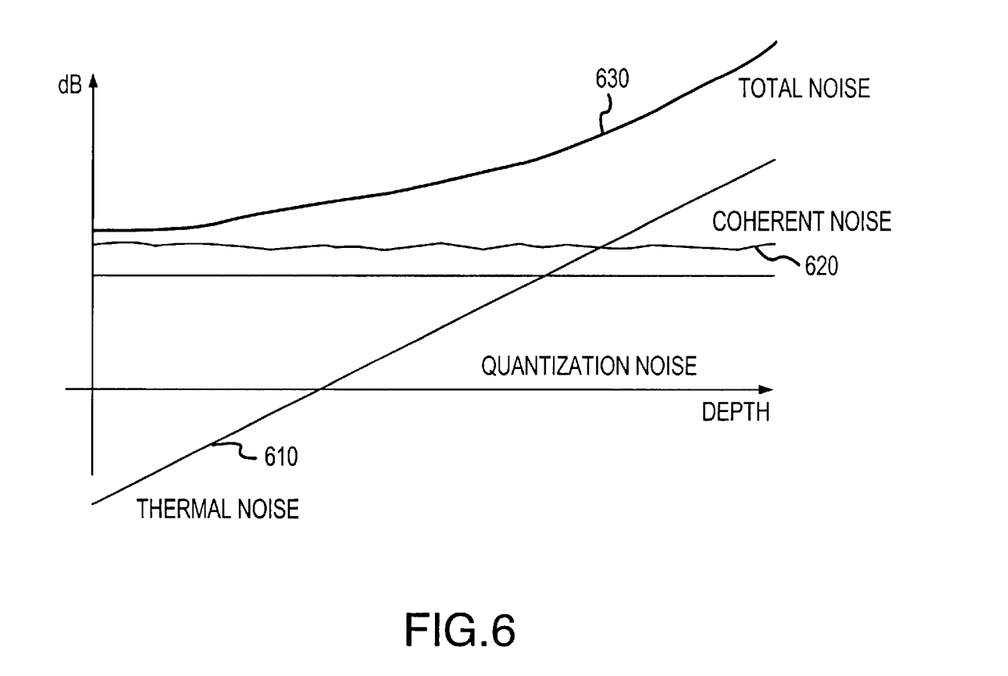
FIG. 6 is a graph depicting an example of the actual variation of a noise signal as a function of depth.

FIG. 6 illustrates one sample of an actual noise signal as it varies with increasing scan depth as a result of added gain being applied to compensate for signal attenuation. There is a certain amount of thermal noise 610 which varies somewhat directly as a function of increasing depth. In addition, there is a certain amount of coherent noise 620 which does not vary directly as a function of depth, yet fluctuates randomly with changing depth. This noise level, combined with the more predictable noise level, combines to define a noise signature for that particular examination under existing environmental conditions. As also shown in FIG. 6, as is known in the art, a low-pass filter can be employed to take the combined noise signature and create a smoothly varying noise signature or noise function 630. Nonetheless, this noise function 630 varies from situation-to-situation and moment-to-moment. This is why the prior art ultrasonic imaging system 10 (FIG. 1), which sets the dynamic range based on expected noise levels, does not necessarily use the optimal dynamic range because what dynamic range is optimal potentially varies with each and every scan and scanning situation.

Figure 7:
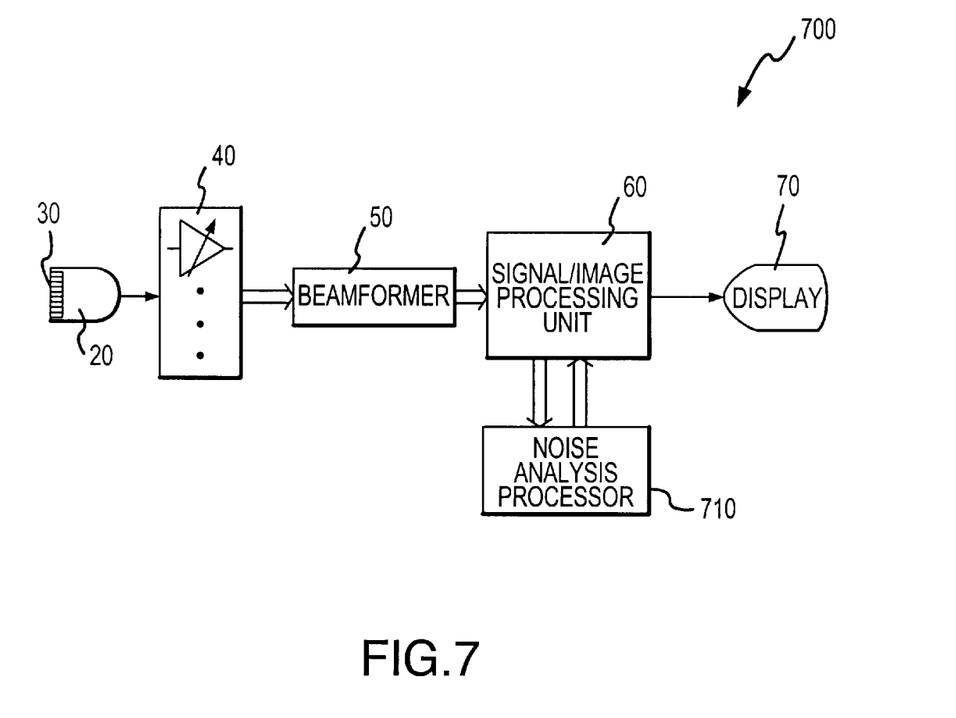
FIG. 7 is a block diagram of an embodiment of the present invention of an ultrasonic imaging system including an apparatus and a method for compressing the dynamic range based on a perceived noise signals.

FIG. 7 depicts one embodiment of an ultrasonic imaging system 700 constructed in accordance with the present invention. The ultrasonic imaging system 700 comprises most of the same components used in the ultrasonic imaging system 10 of FIG. 1. Therefore, in the interest of brevity, these components have been provided with the same reference numerals, and an explanation of their functions and operations will not be repeated. The main difference between the system 700 depicted in FIG. 7 and the prior art system 10 depicted in FIG. 1 is that the system 700 incorporates a noise analysis processor 710 to react to noise actually detected in the patient undergoing the ultrasonic imaging test instead of the compression map select processor 80 (FIG. 1). The noise analysis processor 710 is connected to the signal/image processing unit 60 to facilitate the system 700 responding to actual noise signals.

In the prior art system 10 of FIG. 1, as the transducers 30 were directed by the beamformer 50 to focus imaging pulses toward particular regions of the patient's anatomy, the compression map select processor 80 used the appropriate stored dynamic range map to set the dynamic range that would largely reject ambient noise expected at the region to which the pulses were directed. For example, with regard to the sample dynamic range map of FIG. 5, at a depth of between 1 and 1.5 centimeters, the expected maximum available dynamic range is 75 dB. On the other hand, at a depth of between 2 and 2.5 centimeters, the expected maximum available dynamic range shrinks to 65 dB. Moreover, at the lateral extremes of the scan, between 1 and 1.5 centimeters the dynamic range is compressed to 70 dB, and between 2 and 2.5 centimeters, the dynamic range is compressed to 60 dB. Because this dynamic range is, as is expected in the art, computed on a logarithmic scale, these decreases in potential dynamic range can be significant, for each decrease in dynamic range of 20 dB reflects a tenfold decrease in imaging sensitivity. As noted previously, however, if these expected ranges are either too great or too small, then noise can compromise the image or reduce the potential clarity of the image, respectively.

The disclosed embodiment of the present invention eliminates problems associated with estimating the available dynamic range by actually determining what noise level subsists in different regions of the patient's anatomy. Each region of the patient's body is defined in a coordinate space by the scanning coordinates z, η, and N. The noise analysis processor 710 directs the signal/image processing unit 60 to cause the scanhead to passively scan each region of the patient's anatomy to determine the patient's noise signature as a function of the scanning coordinates. The system 700 passively scans the patient by monitoring signals received with the transducers 30 directed by the beamformer 50 to receive signals from each region, without actively emitting ultrasonic signals. In so doing, the system 700 detects the coherent and random noise detected as a function of the scanning coordinates to build the actual noise signature.

The system 700 not only can discern the actual noise present in the environment of the scan, but, by passively scanning the different regions of the patient's anatomy, the system 700 can adapt for the noise that the system 700 itself generates. The selection and phasing of transducer elements 30, for example, to effect scans at different depths, steering angles, or linear positions, generates a varying degree of noise. The system 700 can take into account the noise generated by the system 700, for that particular examination under existing environmental conditions, to read the actual noise signature and maximize the dynamic range. In sum, embodiments of the present invention can account for actual noise present for a particular examination under existing environmental conditions, including noise subsisting in the imaging system itself. The available dynamic range is set so to the maximum level possible up to, but not including, the level of noise actually detected.

In a preferred embodiment, the operator of the system, can make manual adjustments to the dynamic range. In current systems, the operator has that option so as to be able to allow the system to receive more or less noise so that the operator can be assured that an image of greatest possible content and resolution is being derived. Allowing the operator to make these adjustments can satisfy the operator that the system 700, in optimizing the dynamic range to suppress noise without suppressing useful signals, is actually working.

More specifically, in a preferred embodiment, the useful dynamic range may be determined by subtracting the log of the noise function from the maximum dynamic range setting:

$$d_{\theta,\phi,z} = d_{max} - \log(T[n_{\theta,\phi,z}])$$

It will be appreciated as was previously discussed that, η is a rotational coordinate, N may be either a second rotational coordinate in a sector-type scan or a linear coordinate in a linear-type scan, z is depth, $d_{max}$ is the maximum possible dynamic range applied to the image and may be user selectable, T[ ] represents a low pass filter process, and d as a function of η, N, and z is the actual, available dynamic range for the region of the patient's anatomy as defined by the scanning coordinates.

Figure 8:
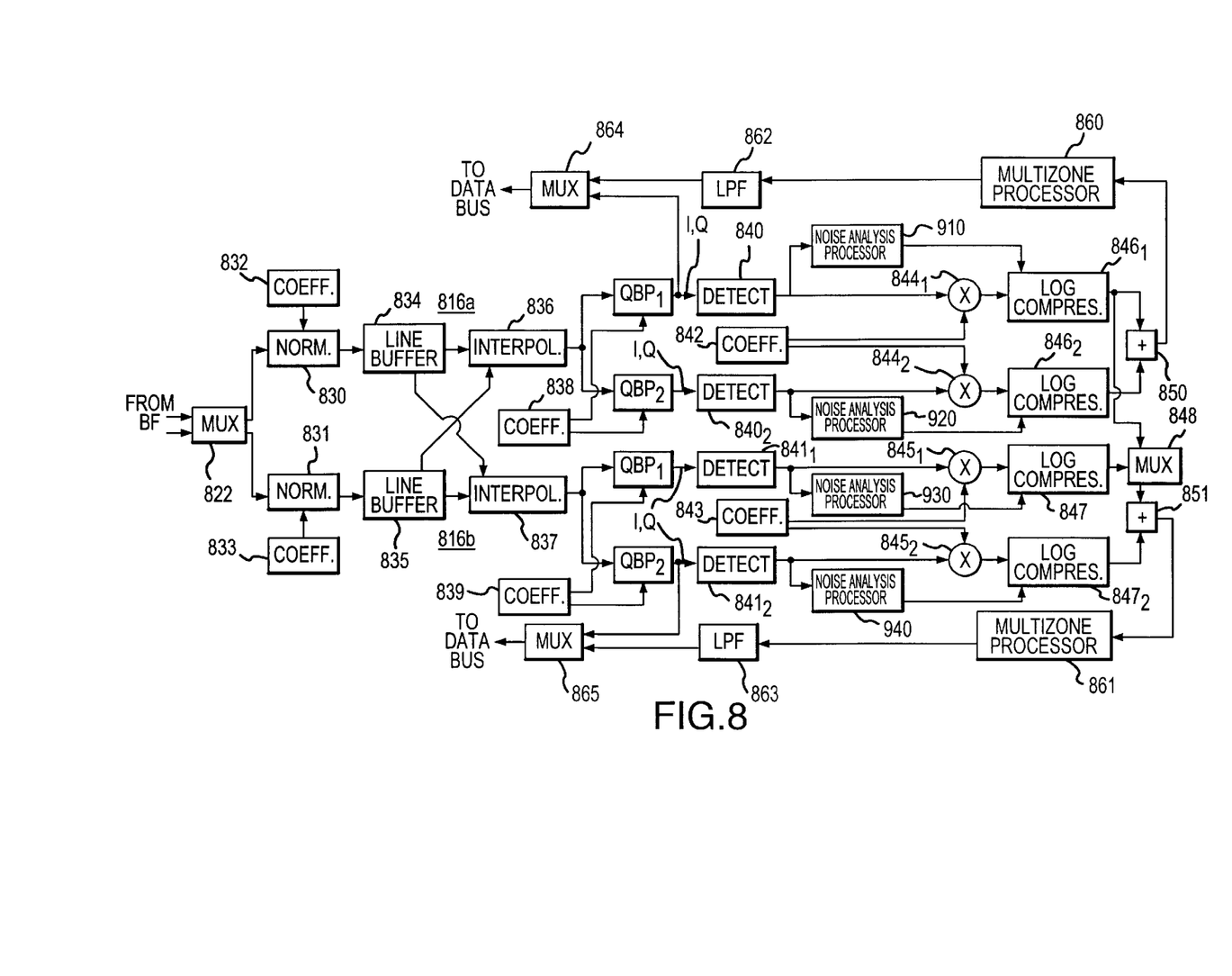
FIG. 8 is a in block diagram of an embodiment of the present invention of an ultrasonic imaging system for a digital multi-channel scanline signal processor including an apparatus and a method for dynamically adjusting the dynamic range in response to an actual detected noise signal.

It will be appreciated that, not only can a noise analysis processor 710 (FIG. 7) be applied to a conventional embodiment of an ultrasonic system, another embodiment of the present invention would include individual noise analysis processors in a digital multi-channel scanline signal processor. Such a multi-channel scanline processor is disclosed in U.S. Pat. No. 6,050,942, which is incorporated herein by reference. As shown in FIG. 8, if the system 816 incorporates separate processing of multiple channels as disclosed in the referenced patent, individual noise analysis processors 910, 920, 930, and 940 could be associated with each channel.

A multi-channel scanline processor 816 is shown in block diagram form in FIG. 8. The signal and data lines connecting the blocks of the block diagram all represent multi-conductor digital data paths, as the scanline processor of the illustrated embodiment is entirely digital. Scanline echo data from the beamformer 814 is applied to a multiplexer 822. When the beamformer produces only a single scanline at a time or scanline data in a time interleaved format, only a single digital data path is needed between the beamformer and the multiplexer 822. In the illustrated embodiment, two digital data paths are shown, enabling two simultaneously generated scanlines to be coupled to the scanline processor 816 in parallel.

The operation of the scanline processor 816 when receiving a single scanline will first be described. The initial data words of the scanline are headers which tell the scanline processor how scanline data is to be received from the beamformer and how it is to be processed. The multiplexer 822 applies the scanline echo data following the headers in parallel to the two channels 816*a*, 816*b* of the scanline processor illustrated in FIG. 8. Each channel of the scanline processor has a normalization stage 830, 831 which multiplies the scanline data by a scale factor on a sample by sample basis to produce gain or attenuation that can vary with depth. The scale factor for each channel is provided by normalization coefficients stored in or generated by coefficient circuits 832, 833, which in a preferred embodiment are digital memories. As the multiplying coefficients are changed along the sequence of scanline echoes, depth dependent gain or attenuation is produced.

Preferably, the coefficient memories 832, 833 store multiple combined gain curves which are changed with memory addressing to match scanhead characteristics or the type of signals being processed (2D or Doppler). The rate of gain change may be controlled by the rate at which the coefficients are changed for the multiplier of each normalization stage 830, 831.

After processing by the normalization stages 830, 831, the echo signals in each channel 816*a*, 816*b* are coupled to line buffers 834, 835. The line buffers perform two functions. First, each line buffer stores the first half aperture beamformed echo signals for synthetic aperture formation. The stored first half aperture signals are combined with the second half aperture signals as the latter are produced to form echo signals from the full synthetic aperture.

Second, the line buffers 834, 835 each store a preceding scanline when the interpolators 836, 837 are operating to interpolate scanline data from consecutively received scanlines. Each of the interpolators 836, 837 interpolates additional scanline data between two received scanlines. In a preferred embodiment two interpolated scanlines are formed between each pair of received scanlines. The two interpolated scanlines are of the form 0.75L.sub.n+0.25L.sub.n+1 and 0.25L.sub.n+0.75L.sub.n+1, where L.sub.n and L.sub.n+1 are consecutively received scanlines. The two interpolated scanlines are located at ¼ and ¾ of the distance from one received scanline to the next. In a preferred embodiment, as described in the aforementioned patent application, each weighted echo sample is saved so that it can be used in the formation of two interpolated scanlines. This results in a reversal of the sequence of interpolated scanline production from one pair of received scanlines to the next. In the preferred embodiment the 0.25 or 0.75 scaling factors are provided by the multipliers of the normalization stages. Stored weighted scanline signals are cross coupled from the line buffer of one channel to the interpolator of the other channel so that the two interpolated scanlines can be produced in unison, one at the output of each interpolator.

In the case where the interpolators 836, 837 are not active and the scanline processor 816 is processing one scanline at a time, the same sequence of scanline echoes is produced at the output of each interpolator, varying only by the different time varying gain factors of the normalization stages of the respective channels 816*a*, 816*b*. The echo signals in each channel are next coupled to quadrature bandpass filters (QBPs) in each channel. The quadrature bandpass filters provide three functions: band limiting the RF scanline data, producing in-phase and quadrature pairs of scanline data, and decimating the digital sample rate. Each QBP comprises two separate filters, one producing in-phase samples (I) and the other producing quadrature samples (Q), with each filter being formed by a plurality of multiplier-accumulators (MACs) implementing an FIR filter. As an echo sample of the scanline data is applied to one input of a digital multiplier 810 a coefficient is applied to the other multiplier input. The product of the echo sample and the weighting coefficient is stored in an accumulator 812 where it may be accumulated with previous products. Other MACs receive the echo samples at different phases and likewise accumulate weighted echo samples. The accumulated outputs of several MACs can be combined, and the final accumulated product comprises filtered echo data. The rate at which accumulated outputs are taken sets the decimation rate of the filter. The length of the filter is a product of the decimation rate and the number of MACs used to form the filter, which determine the number of incoming echo samples used to produce the accumulated output signal. The filter characteristic is determined by the values of the multiplying coefficients. Different sets of coefficients for different filter functions are stored in coefficient memories 838, 839, which are coupled to apply selected coefficients to the multipliers of the MACs.

The coefficients for the MACs which form the I filter implement a sine function, while the coefficients for the Q filter implement a cosine function. For frequency compounding, the coefficients of the active QBPs additionally implement a sync function multiplied by a sine wave at the center frequency of the desired passband. In the instant case, when the scanline processor 16 is operating on only a single scanline at a time, QBP.sub.1 in channel 816*a* is producing I and Q samples of the scanline data in a first, low frequency passband, and QBP.sub.2 in channel 16*b* is producing I and Q samples of the scanline data in a second, higher frequency passband. Thus, the spectrum of the original broadband echo signals is divided into a high frequency band and a low frequency band. To complete the frequency compounding process, the echo data in the passband produced by QBP.sub.1 of channel 816*a* is detected by a detector 40.sub.1 and the detected signals are coupled to one input of a summer 850. In a preferred embodiment detection is performed digitally by implementing the algorithm $(I^2+Q^2)^{1/2}$. The echo data in the complementary passband produced by QBP.sub.2 of channel 816*b* is detected by a detector 140.sub.2 and these detected signals are coupled to a second input of the summer 850. When the signals of the two passbands are combined by the summer 850, the uncorrelated speckle effects of the two passbands will cancel, reducing the speckle artifacts in the 2D image created from the signals.

Each of the two channels is seen to include two QBPs, labeled QBP.sub.1 and QBP.sub.2 in each channel. These QBPs each begin a split of the respective channel into two subchannels, denoted by the subscripts 1 and 2 in each channel. The subchannels accommodate frequency compounding when the beamformer 814 is producing multiple simultaneous scanlines or the interpolators 836, 837 are each producing an interpolated scanline at the same time. In those instances, the data of the scanline being processed in channel 816*a* is separated into two passbands by QBP.sub.1 and QBP.sub.2 of channel 816*a*, the signals of the two passbands are detected by detectors 840.sub.1, 840.sub.2, then combined by summer 850 to produce a speckle reduced scanline at the output of summer 850. Channel 816*b* operates in a similar manner on the scanline data in that channel, using QBP.sub.1 and QBP.sub.2 of channel 816*b* to separate the scanline data into two passbands, detecting the signals in detectors 840.sub.1, 840.sub.2, then combining the detected data to produce a second speckle reduced scanline at the output of summer 850.

At the output of these detectors, in accordance with the present invention and its described operation with regard to the noise analysis processor 710 (FIG. 7) in a single scanline processor, individual noise analysis processors 910, 920, 930, and 940 are interconnected between the detectors 840.sub.1, 840.sub.2, 841.sub.1, and 841.sub.2. The output of each of the individual noise processors 910, 920, 930, and 940 are then fed forward into the log compression processors, 846.sub.1, 846.sub.2, 847.sub.1, and 847.sub.2.

Also following the detector in each subchannel is a gain stage formed by multipliers 844.sub.1, 844.sub.2, 845.sub.1, 845.sub.2 which receive weighting coefficients from coefficient memories 842, 843. The purpose of this gain stage is to partition the balance of analog and digital gains in the ultrasonic system for optimal system performance. Some of the gains in the echo signal path may be automatically implemented by the ultrasonic system, while others, such as the manual gain control and the TGC gain of TGC amplifiers 812, may be controlled by the user. The system partitions these gains so that the analog gains preceding the ADCs of the beamformer are adjusted optimally for the dynamic input range of the ADCs. The digital gain is adjusted to optimize the brightness of the image. The two gains together implement gain control changes effected by the user.

In the preferred embodiment the gain imparted to the scanline signals by the multipliers 844.sub.1, 844.sub.2, 845.sub.1, 845.sub.2 is selected in concert with the gain of the preceding normalization stage 830, 831 in the channel. The gain of each normalization stage is chosen to prevent the attainment of saturation levels in the QBPs, as may occur when strong signals from contrast agents or harmonic imaging are being received. To prevent saturation levels the maximum gain of the normalization stage is controlled, and any reduction imposed by reason of this control is restored by the gain of the succeeding multiplier 844.sub.1, 844.sub.2, 845.sub.1, 845.sub.2.

The gain function provided by these multipliers could be performed anywhere along the digital signal processing path. It could be implemented by changing the slope of the compression curves discussed below. It could also, for instance, be performed in conjunction with the gains applied by the normalization stages. This implementation, however, would eliminate the ability to effect saturation control discussed above. The present inventors have found implementation of this gain function to be eased when provided prior to compression, and in the preferred embodiment by use of a multiplier after detection.

The signals produced by the gain stages 844.sub.1, 844.sub.2, 845.sub.1, 845.sub.2 generally exhibit a greater dynamic range than the display 20. Consequently, the scanline signals of the multipliers are compressed to a suitable dynamic range by lookup tables. Generally the compression is logarithmic, as indicated by log compression processors 846.sub.1, 846.sub.2, 847.sub.1, 847.sub.2. The output of each lookup table is proportional to the log of the signal input value. These lookup table are programmable so as to provide the ability to vary the compression curves, and the brightness and dynamic range of the scanline signals sent on for display.

As discussed above, when each channel 816*a*, 816*b* is processing a separate scanline, compressed, speckle reduced scanline signals are produced at the outputs of summer 850, 851 of the two channels. When the two channels are each processing one passband of the same scanline, a multiplexer 848 couples the signals from the passband formed by QBP.sub.1 of channel 816*a* to summer 851, where the signals are combined with those of the passband formed by QBP.sub.2 of channel 816*b*. When frequency compounding is not active, the detected and compressed broadband echo signals simply pass through the summers without alteration, or may bypass the summers altogether.

The outputs of the summers 850, 851 are coupled to multizone processors 860, 861, where multizone focused scanlines may be formed when this function is selected by the user. The multizone processors store scanline segments from the current transmit focal zone during multizone operation, and as different transmit focal zone segments are received, the multizone processors assemble the segments to form a complete scanline over the depth of interest. The segments can be received in any depth order, with deepest to shallowest being preferred for reduction of artifacts from prior transmit pulses. As the final segment of each scanline is received, the multizone processor sends the full scanline to a lowpass filter 862, 863. These lowpass filters, like the QBPs, are formed by combinations of multiplier-accumulators with variable coefficients, arranged to implement FIR filters, to control the filter characteristic. The lowpass filters provide two functions. One is to smooth the boundaries between scanline segments when multizone operation is employed. A second function is to match the scanline data rate to the vertical line density of the display (not shown), so as to prevent aliasing in the displayed image. The FIR filters perform this function by selectively decimating or interpolating the scanline data.

The processed scanline data is then put onto a data bus for subsequent processing such as scan conversion, and display. A multiplexer 864, 865 at the output of each channel puts scanline data onto the data bus, and can select data from several points in the process for the bus. Scanline data for 2D display is taken from the lowpass filters 862, 863 and put on the bus by the multiplexer. The multiplexer puts the scanline data onto the bus in accordance with the protocol used to negotiate the bus. The multiplexer also adds header data to the beginning of the scanline to identify the scanline data for subsequent processors.

It is to be understood that, even though various embodiments and advantages of the present invention have been set forth in the foregoing description, the above disclosure is illustrative only. Changes may be made in detail, and yet remain within the broad principles of the invention. For example, although the disclosed embodiments adjust dynamic range as a function of the noise as a function of each of the scanning coordinates, it will be understood that dynamic range could be adjusted only as a function of the noise level detected with respect to only one or two of these scanning coordinates. For example, the dynamic range might be adjusted such as only as a function of depth or only as a function of depth and a steering angle, instead of as a function of all three scanning coordinates.

What is claimed is:

1. A system for adjusting the dynamic range for use in an ultrasonic diagnostic imaging system, comprising:
   a noise analysis processor responsive to noise detected at a plurality of scanning regions, the noise analysis processor developing a noise signature corresponding with changing scanning coordinates and determining a maximum available dynamic range based on the noise signature; and
   an ultrasonic processor coupled to the noise analysis processor, the ultrasonic processor having a dynamic range that is adjusted as a function of the determined maximum available dynamic range.

2. The system of claim 1 wherein the scanning coordinates comprise scanning depth.

3. The system of claim 1 wherein the scanning coordinates comprise linear position.

4. The system of claim 1 wherein the scanning coordinates comprise steering angle.

5. The system of claim 1 wherein the noise processor records the noise detected with changing scanning coordinates to create a noise signature corresponding with the changing scanning coordinates.

6. The system of claim 5 wherein the noise processor further comprises a low-pass filter through which detected noise passes to create a smoothly varying noise signature.

7. The system of claim 6 wherein the noise analysis processor determines the smoothly varying noise signature by calculating a logarithm of the noise signature and subtracting it from a logarithm of a maximum attainable dynamic range setting.

8. The system of claim 1 wherein the noise analysis processor comprises a multiple channel ultrasonic processor adapted for use with a multiple channel ultrasonic imaging system.

9. An ultrasonic diagnostic imaging system, comprising:
   an ultrasonic scanhead having a plurality of transducer elements;
   a plurality of gain control amplifiers coupled to the scanhead for controllably amplifying signals corresponding to echoes of ultrasonic pulses detected by the scanhead;
   a beamformer applying transmit signals to the transducer elements and receiving echo signals from the gain control amplifiers at a plurality of scanning coordinates;
   a noise analysis processor responsive coupled to the gain control amplifiers and responsive to passive noise detected at a plurality of scanning regions, the noise analysis processor developing a noise signature corresponding with changing scanning coordinates and determining a maximum available dynamic range based on the noise signature;
   a signal/image processing unit coupled to receive and process the echo signals to create a multi-dimensional image of a region of the patient's body being scanned and using a dynamic range that is adjusted as a function of the determined maximum available dynamic range; and
   a display coupled to the signal/image processing unit for displaying the multidimensional image of the region of the patient's body being scanned.

10. The system of claim 9 wherein the scanning coordinates comprise scanning depth.

11. The system of claim 9 wherein the scanning coordinates comprise linear position.

12. The system of claim 9 wherein the scanning coordinates comprise steering angle.

13. The system of claim 9 wherein the noise processor records the noise detected with changing scanning coordinates to create a noise signature for corresponding with changing scanning coordinates.

14. The system of claim 13 wherein the noise processor further comprises a low-pass filter through which detected noise passes to create a smoothly varying noise signature.

15. The system of claim 14 wherein the noise analysis processor determines the smoothly varying noise signature by calculating a logarithm of the noise signature and subtracting it from a logarithm of a maximum attainable dynamic range setting.

16. The system of claim 9 wherein the noise analysis processor comprises a multiple channel ultrasonic processor adapted for use with a multiple channel ultrasonic imaging system.

17. A method for ultrasonic diagnostic imaging, comprising:
   detecting noise subsisting in a patient's body, attendant environment and an ultrasonic diagnostic imaging system at the plurality of scanning regions;

developing a noise signature corresponding with varying scanning coordinates based on the passively detected noise;

determining a maximum available dynamic range of the ultrasonic imaging system based on the noise signature; and adjusting the dynamic range used by the imaging system as a function of the maximum available dynamic range.

18. The method of claim 17 wherein the scanning coordinates comprise scanning depth.

19. The method of claim 17 wherein the scanning coordinates comprise linear position.

20. The method of claim 17 wherein the scanning coordinates comprise steering angle.

21. The method of claim 17 wherein the act of developing a noise signature corresponding with the changing scanning coordinates comprises recording noise detected with changing scanning coordinates.

22. The method of claim 21 further comprising low-pass filtering the detected noise to create a smoothly varying noise signature.

23. The method of claim 22 further comprising determining the noise signature by calculating a logarithm of the detected passive noise and subtracting it from a logarithm of a maximum attainable dynamic range setting.

24. The method of claim 17 adapted for a multiple channel ultrasonic imaging system by performing the acts of claim 17 for each channel of the multiple channel ultrasonic imaging system.

* * * * *

UNITED STATES PATENT AND TRADEMARK OFFICE
CERTIFICATE OF CORRECTION

PATENT NO.     : 6,666,824 B2
DATED          : December 23, 2003
INVENTOR(S)    : David Rust and David Roundhill It is certified that error appears in the above-identified patent and that said Letters Patent is hereby corrected as shown below:

<u>Title page,</u>
Item [57], line 5, "and in imaging system" should read -- and in the imaging system --

<u>Column 2,</u>
Line 65, "Dynamic range also" should read -- Dynamic range is also --

<u>Column 3,</u>
Line 42, "can be regarded is the" should read -- can be regarded as the --

<u>Column 4,</u>
Line 55, "exceeds the that" should read -- exceeds that --

<u>Column 7,</u>
Line 9, "to created a" should read -- to create a --
Line 38, "based on a perceived noise signals." should read -- based on perceived noise signals. --
Line 39, "is a in block diagram" should read -- is a block diagram --

<u>Column 8,</u>
Line 30, "1.5 centimeters the dynamic" should read -- 1.5 centimeters, the dynamic --

<u>Column 9,</u>
Line 3, "range is set so" should read -- range is set --
Line 6, "operator of the system," should read -- operator of the system --

UNITED STATES PATENT AND TRADEMARK OFFICE
CERTIFICATE OF CORRECTION

PATENT NO. : 6,666,824 B2
DATED : December 23, 2003
INVENTOR(S) : David Rust and David Roundhill

It is certified that error appears in the above-identified patent and that said Letters Patent is hereby corrected as shown below:

Column 11,
Line 21, "in channel 16*b* is" should read -- in channel 816*b* is --

Column 12,
Line 64, "processors 860, 861, where" should read -- processors 860,861, where --
Line 23, "processor responsive coupled to the gain" should read -- processor coupled to the gain --

Signed and Sealed this

Thirty-first Day of August, 2004

JON W. DUDAS
*Director of the United States Patent and Trademark Office*